(12) United States Patent
Correia Pereira Silva et al.

(10) Patent No.: US 12,138,133 B2
(45) Date of Patent: Nov. 12, 2024

(54) CERAMIC STRUCTURE FOR DENTAL APPLICATION, PROCESS AND ITS USES

(71) Applicant: UNIVERSIDADE DO MINHO, Braga (PT)

(72) Inventors: Filipe Samuel Correia Pereira Silva, Guimarães (PT); Paulo Filipe Salgado Pinto, Guimarães (PT); Óscar Samuel Novais Carvalho, Guimarães (PT)

(73) Assignee: UNIVERSIDADE DO MINHO, Braga (PT)

( * ) Notice: Subject to any disclaimer, the term of this patent is extended or adjusted under 35 U.S.C. 154(b) by 1204 days.

(21) Appl. No.: 16/759,651

(22) PCT Filed: Oct. 26, 2018

(86) PCT No.: PCT/IB2018/058403
§ 371 (c)(1),
(2) Date: Apr. 27, 2020

(87) PCT Pub. No.: WO2019/082159
PCT Pub. Date: May 2, 2019

(65) Prior Publication Data
US 2020/0306019 A1   Oct. 1, 2020

(30) Foreign Application Priority Data

Oct. 26, 2017   (PT) .......................................... 110370

(51) Int. Cl.
*A61C 13/00*    (2006.01)
*A61C 5/20*     (2017.01)
(Continued)

(52) U.S. Cl.
CPC ............ *A61C 13/0022* (2013.01); *A61C 5/20* (2017.02); *A61C 5/77* (2017.02); *A61C 8/00* (2013.01);
(Continued)

(58) Field of Classification Search
CPC ....... B28B 11/12; A61C 8/00; A61C 13/0022; A61C 5/20; A61C 5/77; A61C 13/0004;
(Continued)

(56) References Cited

U.S. PATENT DOCUMENTS 5,902,441 A     5/1999   Bredt et al.
2002/0125619 A1  9/2002   Bodenmiller
(Continued)

FOREIGN PATENT DOCUMENTS

CN      102302381 A    1/2012
DE    102009028666 B3  2/2011
(Continued)

OTHER PUBLICATIONS

Elliot Mechanic, BSC; DDS: "The Zirconia-Based Porcelain Veneer", dentistrytoday.com, Jul. 2012 (Jul. 1, 2012), pp. 102-105.
(Continued)

*Primary Examiner* — Mathieu D Vargot
(74) *Attorney, Agent, or Firm* — Leason Ellis LLP (57) ABSTRACT

The present disclosure relates to a ceramic structure for dental application, preferably dental restoration, process for obtaining it and its uses. The process now disclosed comprises computer-controlled machining (CNC), particularly by milling, to obtain a ceramic structure, for example dental covers, which reach thicknesses between 0.05 and 0.4 millimeters.

13 Claims, 3 Drawing Sheets

(51) Int. Cl.

| | | |
|---|---|---|
| *A61C 5/77* | (2017.01) | |
| *A61C 8/00* | (2006.01) | |
| *A61C 13/08* | (2006.01) | |
| *A61C 13/083* | (2006.01) | |
| *A61K 6/802* | (2020.01) | |
| *A61K 6/804* | (2020.01) | |
| *A61K 6/813* | (2020.01) | |
| *A61K 6/818* | (2020.01) | |
| *B28B 11/12* | (2006.01) | |
| *C04B 35/64* | (2006.01) | |
| *C04B 41/00* | (2006.01) | |
| *B28B 3/02* | (2006.01) | |

(52) U.S. Cl.
CPC ........ *A61C 8/0019* (2013.01); *A61C 13/0004* (2013.01); *A61C 13/082* (2013.01); *A61C 13/083* (2013.01); *A61K 6/802* (2020.01); *A61K 6/804* (2020.01); *A61K 6/813* (2020.01); *A61K 6/818* (2020.01); *B28B 11/12* (2013.01); *C04B 35/64* (2013.01); *C04B 41/009* (2013.01); *A61C 2201/002* (2013.01); *B28B 3/02* (2013.01); *C04B 2235/612* (2013.01); *C04B 2235/6562* (2013.01); *C04B 2235/6567* (2013.01)

(58) Field of Classification Search
CPC .... A61C 13/082; A61C 13/083; A61K 6/813; A61K 6/804; A61K 6/802; A61K 6/818
See application file for complete search history.

(56) References Cited

U.S. PATENT DOCUMENTS

| | | | |
|---|---|---|---|
| 2005/0110177 A1* | 5/2005 | Schulman | A61C 13/0003 264/16 |
| 2006/0099552 A1 | 5/2006 | Van Der Zel | |
| 2009/0115084 A1 | 5/2009 | Moon | |
| 2013/0224688 A1 | 8/2013 | Mayr et al. | |
| 2017/0156828 A1* | 6/2017 | Leeson | A61C 13/0022 |

FOREIGN PATENT DOCUMENTS

| | | |
|---|---|---|
| DE | 102005056565 B4 | 5/2013 |
| GB | 2488967 A | 9/2012 |
| JP | 2017035458 A | 2/2017 |
| KR | 20110059972 A | 1/2007 |
| WO | WO 2008/062938 A1 | 5/2008 |
| WO | WO 2011/003612 A1 | 1/2011 |

OTHER PUBLICATIONS

Fernando Zorone; Simona Russo; Roberto Sorrentino, From Porcelain Fused-to-Metal to Zirconia: Clinical and Experimental Considerations, Dental Materials, vol. 2, No. 7, 2011, pp. 83-96.

Willer J. et al., Computer-assisted milling of dental restorations using a new CAD/CAM data acquisition system, in: Journal of Prosthetic Dentistery, vol. 8, pp. 346-353, 1998.

Moustafa N.A. et al., Internal adaptation, marginal accuracy and microleakage of a pressable versus a machinable ceramic laminate veneers, in: Journal of Dentistry, vol. 40, pp. 670-677, 2012.

Alghazzawi T.F. et al., Advancements in CAD/CAM technology: Options for practical implementation, in: Journal of prosthodontic research, vol. 60, pp. 72-74, 2016.

* cited by examiner

CERAMIC STRUCTURE FOR DENTAL APPLICATION, PROCESS AND ITS USES

CROSS-REFERENCE TO RELATED APPLICATIONS

This application is a U.S. National Stage Application under 35 U.S.C. § 371 of International Patent Application No. PCT/IB2018/058403, filed Oct. 26, 2018 which claims priority to Portugal Patent Application No. 110370, filed Oct. 26, 2017, the contents of which are each hereby incorporated by reference in their respective entireties.

TECHNICAL DOMAIN

The present disclosure relates to the aesthetic application of dental ceramics, preferably dental ceramic aesthetic restoration, particularly to the obtention of a ceramic structure with a thickness between 0.05 and 0.4 millimeters for partial coating of a tooth.

BACKGROUND

The dental application is carried out essentially by metal-ceramic structures that comprise ceramic or porcelain coatings for aesthetic appearance.

Dental covers—comprising porcelain/ceramic covers and resin covers—are very thin prostheses that are glued or cemented in front of the teeth, previously worn or discolored, or damaged, in order to provide those with a natural appearance, as well as to promote resistance comparable to natural tooth enamel.

Dental covers may further be referred to as veneers or facets.

According to that indicated in US 2013/0224688, the processes of manufacturing dental covers are essentially manual, by using the addition of successive layers of ceramic pastes followed by sintering. Alternatively, these may be performed by powder pressing techniques (US 2006/0099552) or by 3D printing processes (U.S. Pat. No. 5,902,441), among other varied processes.

With the advent of numerical controlled (CNC) machining, from computer-aided drawings (CAD), veneers can be produced this way, using subtractive processes, namely milling. This process is widely used to obtain dental components among which dental bridges, implants and parts of dental restorations, made of metallic materials such as Ti, CoCr, stainless steel, or ceramic materials such as ceramics based on zirconia, alumina, among others. In the case of ceramic materials of high mechanical strength and hardness, machining is usually performed in "green" state e.g. on a compact of powders which may or may not have been subjected to a pre-sintering to create a better bond between the ceramic powders, but without the compact being completely (i.e. in its entirety) sintered. In the literature it is reported that it is very difficult to machine thin covers from pressed blocks, possibly pre-sintered, (Fernando Zarone*, Simona Russo, Roberto Sorrentino, *From porcelain-fused-to-metal to zirconia: Clinical and experimental considerations, dental materials,* 2 7 (2011) 83-96), with minimum thicknesses being mentioned, which are possible of being machined by CNC, of approximately 0.4-0.5 millimeters. The reason for the difficulty in the use of machining is linked to the mechanical strength of the cover, while it is not completely sintered, that is, it is still "green", and it is not able to withstand machining forces during the milling process. Obtaining covers with thicknesses in the order of 0.4-0.5 millimeters results in relatively thick tooth covers requiring a substantial thinning of the tooth, in the same order of magnitude of the thickness of the cover, for subsequent application of the cover over the previously thinned tooth. This process of substantial tooth thinning is rather time-consuming, invasive, and causes great discomfort in the client. The covers to be applied should have the smallest thickness possible, in order to avoid great thinning of the tooth. There is also the possibility of machining ceramic pieces, from blocks already totally sintered, obtaining minimum thicknesses of up to 0.2 millimeters (Elliot Mechanic, BSc, DDS, *The Zirconia-Based Porcelain Veneer, DENTISTRYTODAY.COM*, JULY 2012, p. 102-105). However, the thinning of sintered zirconia is a rather time-consuming process and requires rather expensive equipments and is therefore not an acceptable process for industrializing the processing of these covers.

The "green" machining process, that is, over a compact of powders, which has been subjected to a possible pre-sintering, but not completely sintered, is particularly useful because it allows high machining rates, quickly, and obtaining very strict geometries, without deviations from the initial drawings in CAD, using relatively inexpensive CNC milling equipments when compared to equipments for milling sintered components. However, this process has the disadvantage that the compact of powders is fragile and can fracture easily during machining, especially when the thickness of the covers or other components, to be machined, or some areas thereof, is small, usually when it is less than 0.4 or 0.5 mm.

The present disclosure presents a new process, wherein the ceramic cover to be "green" machined is, throughout the entire machining process, supported on the face opposite to the machining face by another support material, and in which, in the final phase of the machining, the support material allows to cushion any impacts between the milling cutter and the part, derived from the machining process. The machining form proposed in this document allows the obtention of ultrathin covers or veneers obtained by machining blocks of pressed powders and optionally pre-sintered. This proposal presents itself as much more efficient than the existing processes as it allows to obtain ultrathin covers by numerical controlled machining (CNC), from blocks of powders, possibly pre-sintered, avoiding that the ceramic covers, when they are very thin, fracture during the machining process. This enables the processes for preparing the teeth before receiving these covers, to be minimally invasive, with a very small thinning of the tooth, in the order of magnitude of the thickness of the covers, that is, between 0.05 and 0.4 millimeters.

These facts are described in order to illustrate the technical problem addressed by the present disclosure.

General Description

The present disclosure relates to a process of manufacturing ultrathin dental covers of ceramic material, preferably of zirconia or alumina or zirconia or alumina-based materials, wherein the zirconia may contain stabilizing elements of the tetragonal phase of zirconia such as yttria, ceria, magnesia, among others, or zirconia and alumina each may have oxides or other miscellaneous compounds that are responsible for color, or even fluorescence, and which are applied in the restoration or for aesthetics purposes of teeth.

Dental covers may also be referred to as ultrathin veneers, blades or facets.

As previously mentioned, the ultrathin dental covers are intended to be applied to teeth having essentially an aesthetic function (to provide those with a natural appearance) but they should also have mechanical resistance to wear and abrasion, as well as physical properties such as color, translucency or fluorescence.

The purpose of the cover being ultrathin is to render the process minimally invasive, i.e. to prevent the tooth on which the cover is being applied from suffering a high level of thinning or removal of material from the tooth surface. The thickness of enamel to remove from the surface of the tooth, carried out with tools such as small mills, is usually of the order of magnitude of the thickness of the cover to be applied to the tooth.

The covers obtained by this novel process have a thickness which may range between 0.05 and 0.4 millimeters.

The developed process allows a computer-controlled machining manufacture (CNC), in particular by milling, and a fastening of the component to be milled, during the machining sequence. Milling is a process of mechanical machining, made by milling machines and special tools called milling cutters. Milling consists of the removal of material from the surface of a part, so that the end piece reaches the desired shape and finish. During milling, the removal of material from the part is done by combining several simultaneous movements: rotation of the tool, milling cutter, and translation and rotation movements of the milling cutter holder and the machine table, where the part to be machined is fixed.

The present disclosure comprises the following aspects:
in placing 'dampers' between the part to be machined, i.e. the future cover, and the fastening elements (clamps) of the machine or original ceramic block, both rigid and wherein the dampers consist of a low modulus of elasticity material; and
in placing a support material, on the first face of the machined cover, after its machining, covering the whole face, and causing that during the machining of the opposite face, or second face, the first face being machined is supported by the support material. This allows that during the entire machining process, the opposite face of the cover being machined, is completely supported by a support material.

These aspects allow for possible shocks between the cutting tool and the part, derived from vibrations and/or gaps of the equipment or even from errors associated with the software and from possible machining strategies, to be damped and thus minimized, eliminating the effect of the impact between the tool and the part, thus preventing the part, when it already has a very thin thickness, that is, already has dimensions close to the final ones, becoming the ultrathin veneer, from fracturing during the final phase of machining.

The machining is performed on compacts of powders, which may or may not be subjected to an initial pre-sintering, and that, after machining, the cover will be subjected to final sintering for consolidation of the final cover.

The proposal has several advantages. The first great advantage of the process is to allow ultrathin covers to be obtained, being able to reach thicknesses between 0.05 and 0.4 millimeters, using computer-controlled (CNC) machining of pre-compacted powder blocks. Traditionally, ultrathin covers have been obtained by very expensive and time-consuming manual processes, usually in materials poor in mechanical strength, such as porcelains, and additive processes of placing successive layers of ceramic powders are used, followed by sintering, and manual finishing processes such as thinning, polishing, among others, until the desired dimensions are reached. The use of computer-controlled machining is not easily practicable in porcelains. It is, however, possible and easy in materials such as zirconia or alumina, or compounds based on the former as they are presented in compacted blocks, obtained by compacting ultrathin powder agglomerates with about 0.06 millimeters particle size agglomerates of the powder, the powder particles having about 50 nanometers in size. The machining of these pressed blocks is relatively easy because the powder block has not yet been fully densified, thus allowing for an easy, fast, and inexpensive machining.

The second major advantage is to enable said ultrathin covers to be of high strength ceramic materials such as zirconia, alumina, or compounds based on the above-mentioned materials, zirconia or alumina. As referred to in the previous point it is possible to machine by CNC materials with high mechanical and wear resistance provided that these are present in compacts of pressed powders and, possibly, pre-sintered, with dimensions as referred to in the previous point. This will make it possible to obtain the ultrathin covers in materials with mechanical bending strengths of about 1200 MPa, and wear resistance, also very high.

The third great advantage is that the machining can be carried out in 'green machining' powder compacts, which can undergo pre-sintering before being machined, and without these compacts being fractured during machining. Conventional machining in pre-pressed blocks causes very fragile parts because they are not yet completely sintered or densified. The possibility of fracture of these parts during machining is usually high, especially when the parts or zones thereof have thicknesses of less than 0.5 millimeters. The possibility of machining parts with relatively large areas (for example up to 15×15 millimeters) with very thin thicknesses (reaching thicknesses between 0.05 and 0.4 mm) is only possible through this new process.

In this manner, the present disclosure relates to a process for obtaining a ceramic structure for dental application, preferably a ceramic structure for dental restoration, wherein the process comprises the following steps:
machining of a first face of a block of pressed ceramic powders in order to create a cavity in the first face of said block;
inserting a support material into the cavity, so that said material adheres and supports the first face of the block of pressed ceramic powders;
machining of a second face of the block of pressed ceramic powders;
removing the support material, so as to obtain the ceramic structure for dental application, this step being preferably removed by machining.

In one embodiment, the step of inserting the support material into the cavity may be carried out in such a way that said support material preferably adheres and covers the entire first face of the block of ceramic pressed powders and to obtain better results this step can be carried out with the support material in the liquid state.

In one embodiment, the support material may be a low modulus of elasticity material, preferably it is a material with an elasticity of between 0.05-20 GPa, most preferably the support material is a wax or a thermoplastic polymer, or combinations thereof, wherein the thermoplastic polymer may be selected from the following list: polymethyl methacrylate (PMMA), nylon, low density polyethylene (LDPE), or combinations thereof.

In one embodiment, the block of pressed ceramic powders may be secured to the CNC milling equipment by means of a block of a low modulus of elasticity material, being preferably a material with an elasticity of between 0.05-20 GPa, most preferably the support material is a wax or a thermoplastic polymer, or combinations thereof, wherein the thermoplastic polymer may be selected from the following list: polymethyl methacrylate (PMMA), nylon, low density polyethylene (LDPE), or combinations thereof.

In one embodiment, the now disclosed process may comprise a prior step of securing the block of pressed ceramic powders to a CNC milling equipment.

In one embodiment and for obtaining better results, the low modulus of elasticity material may have an elasticity between 0.05-20 GPa, more preferably the support material is a wax or a thermoplastic polymer, or combinations thereof, wherein the thermoplastic polymer may be selected from the following list: polymethyl methacrylate (PMMA), nylon, low density polyethylene (LDPE), or combinations thereof.

In one embodiment and for obtaining even better results, the support material may be wax or a thermoplastic polymer, or combinations thereof, wherein the thermoplastic polymer is polymethyl methacrylate (PMMA), nylon, low density polyethylene (LDPE), or combinations thereof.

In one embodiment, the block of pressed ceramic powders may comprise zirconia, alumina, or combinations thereof.

In one embodiment, the block of pressed ceramic powders may comprise zirconia, yttria, ceria, magnesia, or combinations thereof.

In one embodiment, the block of pressed ceramic powders may comprise zirconia, alumina, iron oxides, manganese oxides, or combinations thereof.

In one embodiment, the now disclosed process may comprise a step of painting the ceramic structure and/or may comprise a step of cleaning the ceramic structure.

In one embodiment, the process now disclosed may comprise a step of removing the support material, in particular the low modulus of elasticity material.

In one embodiment, the step of removing the support material, in particular the low modulus of elasticity material is performed, by melting or sublimation, at a temperature between 80-400° C.

In one embodiment, the step of removing the support material, in particular the low modulus of elasticity material, is performed by chemical dissolution using a solvent, preferably ethanol.

In one embodiment, the process now disclosed may comprise a step of sintering the ceramic structure with thermal cycles between 1200-1600° C. for 0.5-3 h and between periods of heating and cooling of 2-4 h, with heating ramps of 5° C./minute.

In one embodiment, the step of securing the block of pressed ceramic powders to a CNC milling equipment can be performed by means of fastening elements, preferably by a clamp or a screw.

In one embodiment, the block of pressed ceramic powders may be pre-sintered.

The present disclosure also relates to a ceramic structure for dental application, preferably for dental restoration, obtainable by the process now disclosed, said ceramic structure having a thickness between 0.05-0.4 mm.

In one embodiment, the ceramic structure is a dental cover, a dental facet, a dental blade, an ultrathin dental veneer or implant.

The present disclosure further relates to the use of a support material for producing a ceramic structure for dental application, wherein the support material is a low modulus of elasticity material, in particular with an elasticity between 0.05-20 GPa, wherein said material may be selected from wax, thermoplastic polymer, or combinations thereof.

In one embodiment, the thermoplastic polymer may be polymethyl methacrylate (PMMA), nylon, low density polyethylene (LDPE), or combinations thereof.

BRIEF DESCRIPTION OF THE DRAWINGS

For an easier understanding, the following drawings are attached, which represent preferred embodiments which are not intended to limit the object of the present description.

FIG. 4—a)—Schematic representation of the machining, with milling cutters (5), of the ceramic connection (8) between the cover and the initial block of compact powders, wherein the ceramic connections or supports between the area from where the cover will be removed (4) and the remaining block of ceramic compact (1), are removed, the cover being supported only on the low modulus of elasticity addition material (6). After removal of these ceramic connection, the machining of the second face of the cover (9) takes place, until very thin thicknesses are reached. In this last stage of machining of the cover, this is being supported only by the addition material, for example wax, which is itself supported on the remaining pre-sintered ceramic block; b)—Schematic representation of the machining, with milling cutters, (5) of the second face of the cover (9), in the small block of compacted powders, inserted in or on the surface, and rigidly attached only to the addition material and in the larger block of low modulus of elasticity material, until very thin thicknesses are obtained; c) Detail of the damping effect, with deformation in the elastic regime, of the addition material (6), of low modulus of elasticity, which connects the cover (4) to the main ceramic block (1), or, in the case of the block (18), connects the cover (4) to the clamps—fastening element (19).

DETAILED DESCRIPTION

The present disclosure relates to a method of manufacturing ultrathin dental veneers, blades, facets or covers with thicknesses between 0.05 and 0.4 mm and overall cover dimensions that may reach at least 15 mm in width and in length. These covers are made up of ceramics, preferably of zirconia or alumina or zirconia or alumina-based compounds, wherein the zirconia may contain stabilizing elements of the tetragonal phase of zirconia such as yttria, ceria, magnesia, among others, or zirconia or alumina may contain oxides or other miscellaneous compounds which are responsible for the color and fluorescence, such as iron oxides, manganese oxides, among others, and which are applied in the restoration or for aesthetic purposes of teeth.

The process that allows to obtain ultrathin covers, that is, covers with thicknesses which may be between 0.05 and 0.4 millimeters, comprises manufacturing by computer-controlled machining (CNC), in particular by milling, and in the process of fixing the component to be milled, during the machining sequence.

The present disclosure relates to a process for obtaining a ceramic structure either for dental application, preferably dental restoration, or characterized by obtaining a structure with thicknesses between 0.05 and 0.4 millimeters by computer-controlled machining (CNC) and may comprise the following steps:
- placing blocks with a diameter between 85 and 100 millimeters and a thickness between 10 and 20 mm in the CNC milling equipment (5);
- fixing the block to the equipment by fastening elements (19);
- machining one of the faces of the block so that the first face of the cover is formed (4);
- inserting into the cavity existing after the previous step, a low modulus of elasticity material, that adheres either to the block and to the machined face of the cover;
- starting to machine the second face of the cover (9) on the other side of the block and removing the ceramic connections before reaching a thickness of 0.5 mm, the cover then being supported exclusively on the low modulus of elasticity material;
- proceeding with the program of machining the cover to reduce the thickness of the cover to the desired dimensions for the cover;
- machining the support material with low modulus of elasticity to separate the cover from the block, the cover still coming together with the low modulus of elasticity material on one side;
- placing the cover in a furnace or in a chemical solution to remove the low modulus of elasticity material;
- sintering the cover in a thermal cycle of temperatures between 1200 and 1600° C. for a period of time between 0.5 and 3 hours, between heating and cooling periods, which can last between 2 to 4 hours, with heating ramps of about 5° C./minute.

In one embodiment, the block may be a compact of ceramic powders or block of material having a low modulus of elasticity which incorporates in its interior and surface one or more compact blocks of ceramic powders of smaller dimensions.

In one embodiment, the compact block of ceramic powders of smaller dimension may be between 10 and 20 millimeters in diameter and about 3 millimeters in thickness.

In one embodiment, the compact blocks of ceramic powders may be of zirconia or alumina or zirconia or alumina-based compounds, wherein the zirconia may contain stabilizing elements of the tetragonal phase of zirconia such as yttria, ceria, magnesia, among others, or the zirconia or alumina may contain oxides such as iron oxides, manganese oxides, among others.

In one embodiment, the low modulus of elasticity material may have between 0.05 and 20 GPa.

In one embodiment, the low modulus of elasticity material of the block may be thermoplastic wax or polymer such as PMMA, Nylon, LDPE, among others.

In one embodiment, the fastening elements may be clamps or screws, among others.

In one embodiment, in the final machining step of the second face of the cover, the cover is supported on the entire first face of the cover being machined by the low modulus of elasticity material, and the connection between the cover and the larger block is through material of low modulus of elasticity.

In one embodiment, the placement of the low modulus of elasticity material in the cavity can be carried out by pouring in the liquid state.

In one embodiment, the removal of the wax or of other low modulus of elasticity material, can be carried out in a furnace having a temperature between 80° and 400° C.

In one embodiment, the chemical solution may consist of a solvent such as ethanol, or another equivalent, or other chemical dissolution agent, in the case of other polymers.

In one embodiment, the dental covers may have a thickness between 0.05 and 0.4 millimeters and lengths of at least 15 millimeters and widths of at least 15 millimeters.

Figure 1:
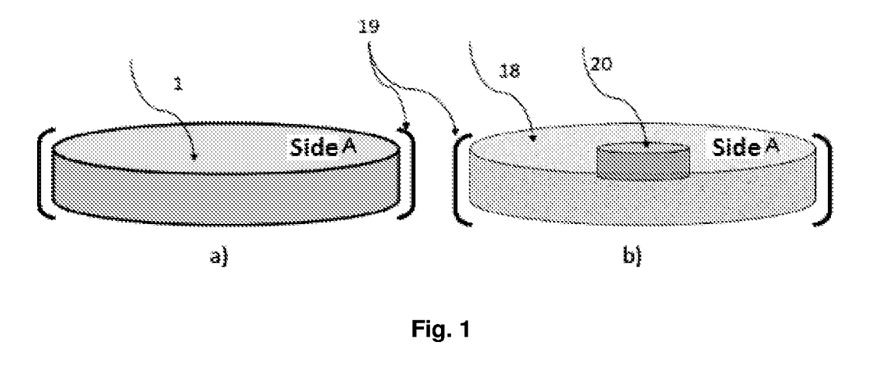
FIG. 1 a)—shows an example of a block of pressed ceramic powders (1) and optionally pre-sintered, placed on the fastening elements (19) of the machine; b)—shows a block (18) in a low modulus of elasticity material, in which small blocks (20) of pressed ceramic powders of the same material as the disc (1) are rigidly fixed in its interior and to the surface, the first (18) being placed in the fastening element of the machine (19).

In one embodiment, the process may be initiated with a compact block of ceramic powders (1), and which is to be fixed by fastening elements (19) of the machine, such as for example, clamps, screws, or other fastening elements of the block in the machine, which can be sold commercially, or which may be obtained by compacting powders, made in a press, in a mould, with pressures that can oscillate between 30 and 200 MPa. Pressed blocks are usually pre-sintered at temperatures that can oscillate between 600° C. and 1100° C., for periods ranging from 1 hour to 12 hours, and wherein the dimensions of the blocks are normally between 85 and 100 millimeters in diameter, with a thickness between 10 and 20 millimeters. Pre-sintering may slightly increase the resistance of the pressed and during machining it can increase the wear of the cutting tools. Alternatively, blocks of low modulus of elasticity material may be used (18), for example of wax or other polymer, which will be fixed with the fastening elements (19) to the machine, and are therein embedded (i.e., inserted inside and on the surface) and rigidly fixed, small blocks of pressed ceramic powders (20), of the same material of block 1, and with dimensions between 10 and 20 millimeters—a little larger than the dimensions of the final cover to be obtained from these small blocks. As an example, it can have 20 millimeters in diameter and 3 millimeters in thickness. The wax or polymer blocks (18), may be commercially acquired or obtained by melting the low modulus material and subsequent moulding. The small compact blocks of ceramic powders (20) follow the same processing mentioned for block 1, mentioned above.

In one embodiment, blocks (1) or (18) may then be secured to the CNC milling equipments, with metal clamps (19), commercially available, which fix them rigidly, with precision and accuracy.

It can thus be seen that it is possible to use two approaches of fixing the ceramic blocks:
  the ceramic blocks (1) are fixed directly on the metal clamps (19); or
  smaller ceramic blocks (20) are placed and rigidly fixed, mechanically or by means of gluing (for example with material equal to that of the bigger block) onto larger blocks of low modulus of elasticity material (18) and the latter are placed in the machine, fixed by the fastening elements (clamps) (19). With this second option it is achieved that the small ceramic blocks (20) are already supported on a larger block of low modulus of elasticity material (18) and therefore already have some damping effect on the connection between these small ceramic blocks (18) and the machine clamps (19).

Figure 4:
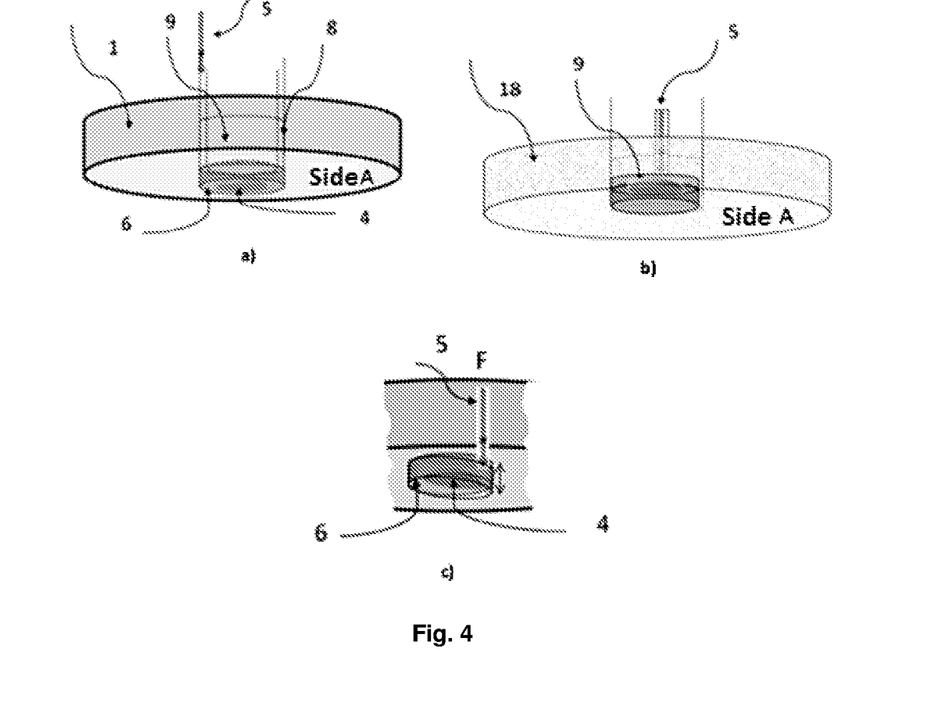

In the first option, before finishing the machining of the second face of the cover, it is necessary to remove the ceramic connection between the initial ceramic block (1) and the small block from where the cover (4) will be extracted, the cover being connected to the main ceramic block (1) only through material of low modulus of elasticity, thus gaining damping capacity (FIG. 4c)), with elastic deformation of the addition material, necessary for the cover not to fracture during the final phase of machining. In both cases, during the final phase of machining, besides these dampers for the cover, it also has support material that covers the entire face that was the first to be machined.

Figure 2:
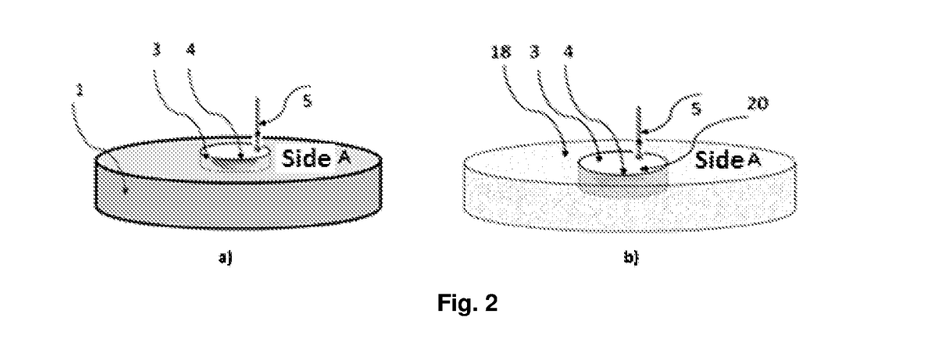
FIG. 2—a)—schematic representation of the machining, for example with milling cutters (5) of a zone of one face of the block (side A) and of the first face of the cover (4), in the pre-compacted block (1), creating a machined zone (3) around the cover in the ceramic powder compact (1); b) schematic representation of the machining, for example with milling cutters (5) of the first face of the cover (4), in the smaller block of compacted powders (20), embedded in the face A of the block of low modulus of elasticity material (18).

In one embodiment, thereafter, and in both cases of assembly of the ceramic blocks, the numerical program begins to perform the machining, with milling cutters (5), by numerical control, of one of the faces of the cover (4).

Figure 3:
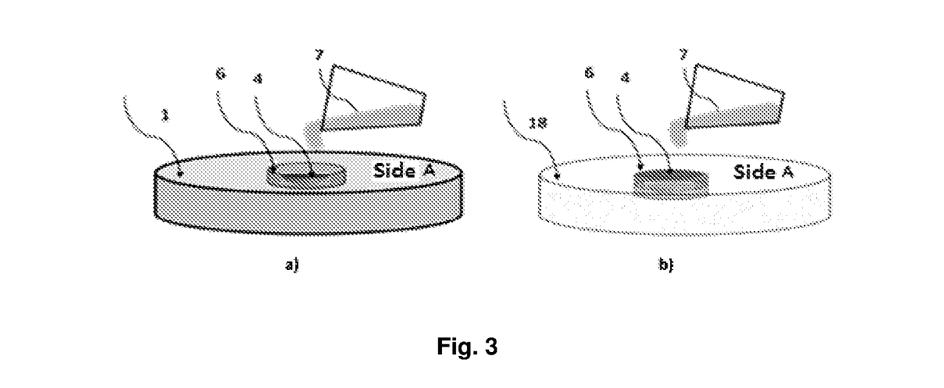
FIG. 3—a) and b)—Schematic representation of the filling process (6) of the hole and of the area of the first face of the cover (4), already machined, for example by pouring wax in the liquid state (7) with a low modulus of elasticity material such as wax, or another polymer.

In one embodiment, after the first face (4) (Side A) of the cover is machined, the process is interrupted, and the cavity (3) relating to the cover made in the compact due to the machining of this face of the cover, is filled (6) with a material such as wax or other polymer having a low modulus of elasticity (typically between 0.05 and 20 GPa), and that adheres either to the block of ceramic powders (1) or block of low modulus of elasticity material (18), and to the machined face of the cover (4). This filling can be, for example, by pouring in the liquid state (7) wax, or thermoplastic polymers as PMMA-Poly (methyl methacrylate, Nylon, LDPE—Low-density polyethylene, among others.

In one embodiment, the equipment then starts the machining (5) of the other face of the cover (9) on the other side of the compact block, and in the case of the compact block of ceramic powders (1), removes the ceramic connections (8) between the cover and the initial ceramic block (1), before the cover reaches very thin thicknesses, for example before it reaches about 0.5 mm of thickness.

In one embodiment, the equipment then proceeds the program of machining the second face of the cover (9) until the cover reaches the desired ultrathin thickness, i.e. between 0.05 and 0.4 millimeters. During this final stage of machining of the cover, the cover is connected to the ceramic block (1) or to the block of low modulus of elasticity material (18), only by the addition material (6), which gives it a damping effect, with elastic deformation of the addition material and, in the case of the disc (18), also of the disc itself (18), as schematically shown in FIG. 4c), for example when there is an impact (F) of vibration of the milling cutter (5) relative to the cover (4). In addition, the first face of the cover to be machined (4) is also fully supported by the addition material (6), which also gives it a damping effect and additional resistance of the cover, when subjected to loads (F) of impact or machining. The fact that the support material of the cover as well as the connection material of the cover in relation to the initial blocks (1) (18) has low a modulus of elasticity, allows any impact between the milling cutter (5) and the cover to be damped by the low modulus material, thus avoiding this to fracture.

Figure 5:
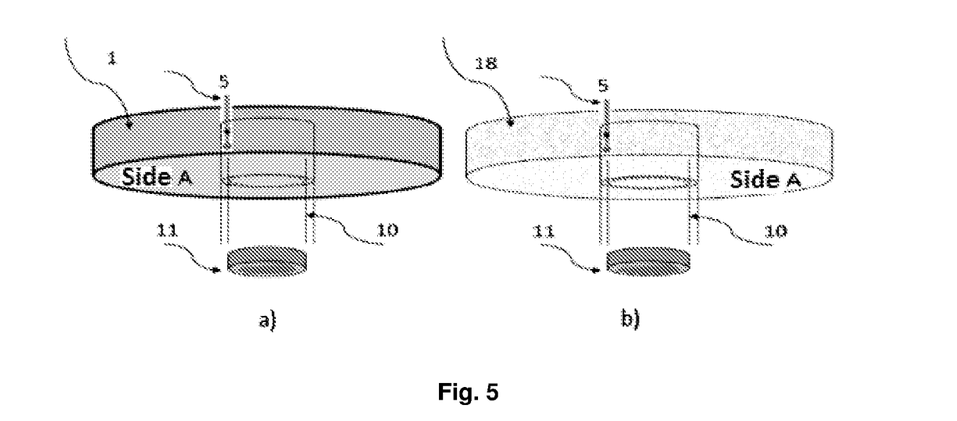
FIG. 5—a) and b)—Schematic representation of the machining (5) of the support (10) in wax, which connects the already fully machined cover to the initial compact block (a) of ceramic or of wax or other polymer (b), and consequent removal of a small block of wax that contains the cover (11).

In one embodiment, upon completion of the machining of the cover, the program will machine the low modulus of elasticity support material (10), in order to separate the cover (11) from the ceramic block (1) or from the block of low modulus material (18), wherein the first face of the cover to be machined (4), remains fully sustained or supported on the material of low modulus of elasticity.

Figure 6:
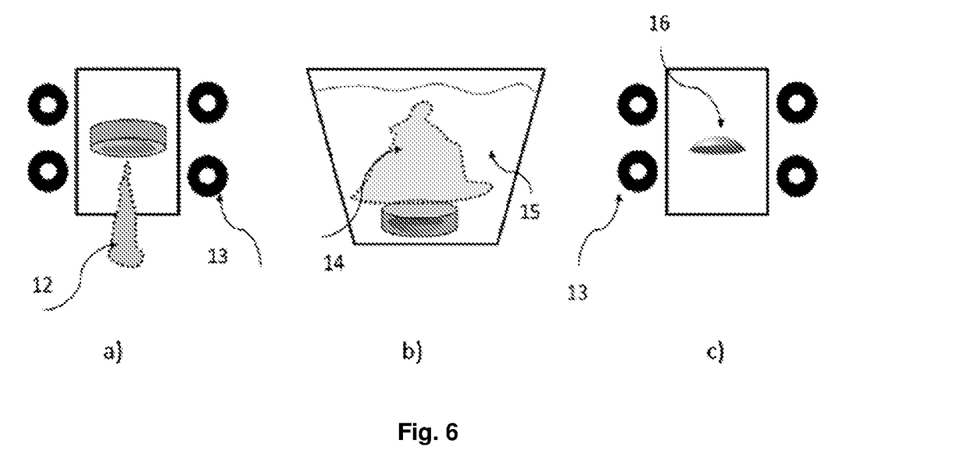
FIG. 6—Schematic representation of the removal of the wax (12) or polymer, (a) by heating (13), or (b) by chemical dissolution (14) in a solvent (15), followed by (c) final sintering of the cover (16) by heating (13) in a furnace.

In one embodiment, thereafter, possible cover paintings, or other treatments such as cleaning may be performed on the exposed face of the cover (9), i.e. on the second face to be machined. After these optional operations, the small block (11), extracted from the main block, composed of the cover and low modulus of elasticity material, which is still attached to one face of the cover, is placed in a furnace for removal of the low modulus of elasticity material (12) by melting or sublimation, under temperatures (13) ranging from 80° C. to 400° C., depending on the low modulus of elasticity material used. Alternatively, the material of low modulus of elasticity, wax or another polymer, can be removed by chemical dissolution (14), in a solvent (15), for example ethanol, in the case of certain waxes, in which case the cover and the material attached thereto should be immersed in said solutions.

In one embodiment, the cover is then placed in a furnace and subjected to final sintering (16), in a thermal cycle that can reach maximum temperatures between 1200° C. and 1600° C. for periods which can last between 0.5 and 3 hours, between periods of heating and cooling, which can last between 2 to 4 hours, with heating ramps of about 5° C./minute.

Figure 7:
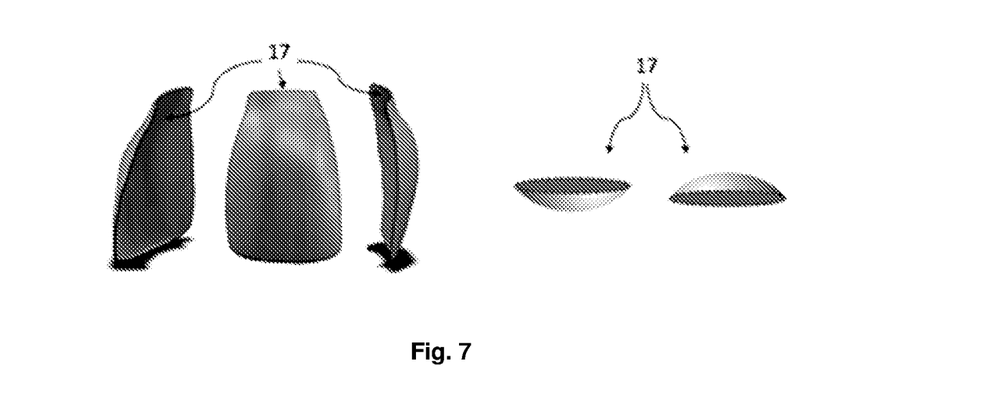
FIG. 7—Schematic representation of the two sides of the cover (17) after final sintering, and having a thickness between 0.05 and 0.4 millimeters.

In one embodiment, after this sintering treatment, the cover (17) is ready and with thicknesses that can be between 0.05 and 0.4 millimeters, and length and width which can reach at least 15 millimeters.

The term "comprises" or "comprising" when used herein is intended to indicate the presence of features, elements, integers, steps and components mentioned, but does not preclude the presence or addition of one or more other features, elements, integers, steps and components, or groups thereof. The present disclosure is not, of course, restricted to the embodiments described herein and a person of ordinary skill in the art may predict many possibilities of modifying it and replacing technical features by equivalent ones, as defined in the appended claims. The described embodiments are combinable with each other. The following claims further define preferred embodiments.

The invention claimed is:

1. A process for obtaining a ceramic structure for dental application, wherein the process comprises the following steps:
  machining a first face of a block of pressed ceramic powders to obtain a first face of the ceramic structure by creating a cavity in the first face of said block;
  inserting a thermoplastic polymeric support material composed of a thermoplastic polymer into the cavity, so that said thermoplastic polymeric support material adheres to and covers the entire first face of the ceramic structure, wherein the thermoplastic polymeric support material supports a portion of the ceramic structure as a ceramic connection;

machining a second face of the block of pressed ceramic powders to form a second face of the ceramic structure;

removing the ceramic connection being the ceramic structure only supported by the thermoplastic polymeric support material;

continuing the machining of the second face of the ceramic structure until a desired dimension of the ceramic structure is obtained; and removing the thermoplastic polymeric support material from the first face of the ceramic structure, to obtain the ceramic structure for the dental application, wherein the thermoplastic polymeric support material is a material having a low modulus of elasticity with an elasticity between 0.05 GPa and 20 GPa, wherein the ceramic structure has a thickness of 0.05 mm, wherein the thermoplastic polymeric is selected from the group consisting of: polymethyl methacrylate (PMMA), nylon, low density polyethylene (LDPE), and combinations thereof, and wherein the ceramic structure is selected from the group consisting of: a dental cover, a dental facet, a dental blade, an ultrathin dental veneer, and an implant.

2. The process according to claim 1, wherein the step of inserting the thermoplastic polymeric support material into the cavity is performed with the thermoplastic polymeric support material in a liquid state.

3. The process according to claim 1, wherein the process comprises, prior to the step of machining the first face of the block of pressed ceramic powders, a step of securing the block of pressed ceramic powders to a computer numerical control (CNC) milling equipment.

4. The process according to claim 1, wherein the block of pressed ceramic powders comprises zirconia, alumina, or both zirconia and alumina.

5. The process according to claim 4, wherein the block of pressed ceramic powders comprises a compound selected from the group consisting of: zirconia, yttrium, cerium, magnesium, and combinations thereof.

6. The process according to claim 4, wherein the block of pressed ceramic powders comprises a compound selected from the group consisting of: zirconia, alumina, iron oxides, manganese oxides, and combinations thereof.

7. The process according to claim 1, wherein the process comprises a step of painting the ceramic structure.

8. The process according to claim 1, wherein the process comprises a step of cleaning the ceramic structure.

9. The process according to claim 1, wherein the step of removing the thermoplastic polymeric support material is performed by melting or sublimation at a temperature between 80-400° C.

10. The process according to claim 1, wherein the step of removing the thermoplastic polymeric support material is performed by chemical dissolution using a solvent.

11. The process according to claim 1, wherein the process comprises a step of sintering the ceramic structure with thermal cycles between 1200-1600° C. for 0.5-3 hours and between periods of heating and cooling for 2-4 hours, with heating ramps of 5° C./minute.

12. The process according to claim 3, wherein the step of securing the block of pressed ceramic powders in the CNC milling equipment is performed using fastening elements.

13. The process according to claim 1, wherein the block of pressed ceramic powders is pre-sintered.

* * * * *